United States Patent [19]

Cook

[11] Patent Number: 4,639,296
[45] Date of Patent: Jan. 27, 1987

[54] METHOD FOR FORMING ETHYLENE GLYCOL FROM SODIUM METHOXIDE

[75] Inventor: Ronald L. Cook, Aurora, Ill.

[73] Assignee: Texaco Inc., White Plains, N.Y.

[21] Appl. No.: 824,811

[22] Filed: Jan. 31, 1986

[51] Int. Cl.$^4$ ............................................... C25C 1/00
[52] U.S. Cl. ...................................................... 204/59 R
[58] Field of Search ...................................... 204/59 R

[56] References Cited

U.S. PATENT DOCUMENTS 4,478,694  10/1984  Weinberg ...................... 204/59 R
4,517,062   5/1985  Barber ........................... 204/59 R Primary Examiner—R. L. Andrews
Attorney, Agent, or Firm—Robert A. Kulason; James J. O'Loughlin; Ronald G. Gillespie

[57] ABSTRACT

Method and apparatus for forming ethylene glycol from sodium methoxide includes combining the sodium methoxide with an anhydrous methanol to provide a mixture. The mixture is then flowed past an anode and then past a cathode. A DC voltage is provided across the anode and the cathode so that the mixture forms ethylene glycol as a product.

8 Claims, 1 Drawing Figure

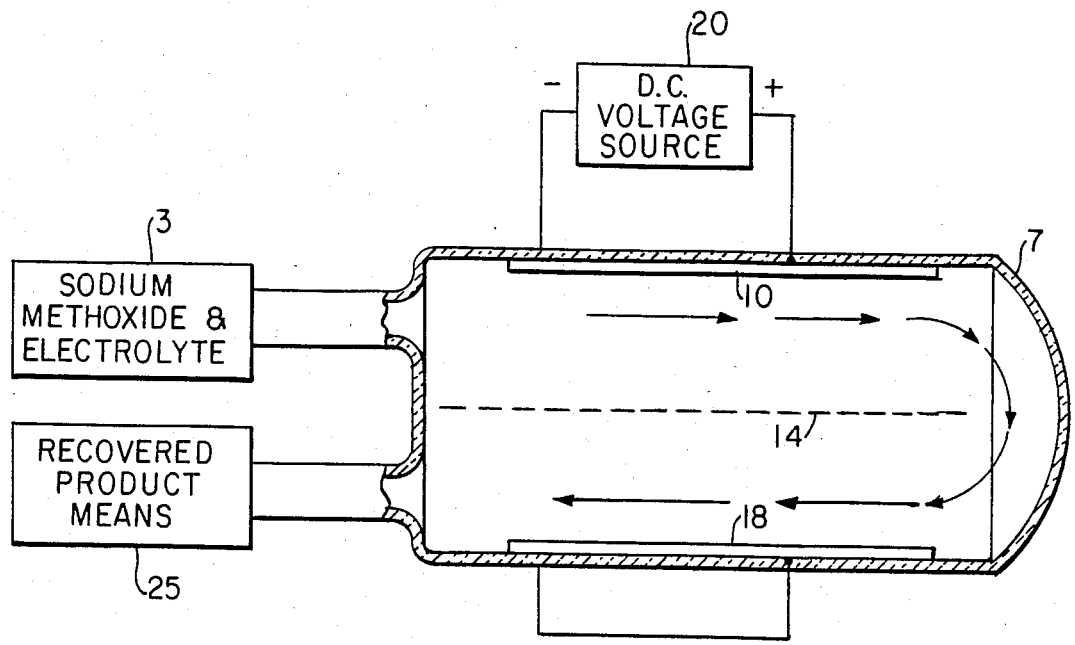

METHOD FOR FORMING ETHYLENE GLYCOL FROM SODIUM METHOXIDE

BACKGROUND OF THE INVENTION

1. Field of the Invention

The present invention relates to electrochemical processes in general and, more particularly, to electrochemical processes and apparatus for forming ethylene glycol.

2. Summary of the Invention

Method and apparatus for forming ethylene glycol from sodium methoxide includes combining the sodium methoxide with anhydrous methanol to provide a mixture. The mixture is then flowed past an anode and then past a cathode. A DC voltage is provided across the anode and the cathode so that the mixture forms ethylene glycol as a product.

The objects and advantages of the invention will appear more fully hereinafter, from a consideration of the detailed description which follows, taken together with the accompanying drawing, wherein one embodiment is illustrated by way of example. It is to be expressly understood, however, that the drawing is for illustrative purposes only, and is not to be construed as defining the limits of the invention.

DESCRIPTION OF THE DRAWINGS

The FIGURE shows a simplified block diagram and reaction cell of apparatus, constructed in accordance with the present invention, for forming ethylene glycol from sodium methoxide.

DESCRIPTION OF THE INVENTION

The present invention, using an electrochemical flow cell oxidizes the methoxy anion (from NaOCH$_3$) to a methoxide radical which undergoes disproportionation to give formaldehyde. The formaldehyde is then carried by the solvent flow to the cathode wherein hydrodimerization can occur on carbon electrodes to give ethylene glycol.

With reference to the drawing, a source 3 provides sodium methoxide (NaOCH$_3$) in anhydrous methanol (CH$_3$OH) to a reaction cell 7. Reaction cell 7 is made of a non-conductive material. An anode 10, preferably made of platinum, an ion exchange nonreactive membrane 14 and a carbon cathode 18, are mounted inside of reaction shell 7. Other materials for anode 10 are ebonex (TiO$_x$) where x can vary between 1.6 and 1.9) which preferably is mostly Ti$_4$O$_7$ with some Ti$_5$O$_9$, and platinum modified titanium. Membrane 14 may be persulfonic acid, which is generally known by its trade name Nafion 117.

Anode 10 and cathode 18 are connected to the positive and negative outputs respectively, of a DC voltage source 20. Membrane 14 is located between anode 10 and cathode 18 and causes the sodium methoxide and electrolyte to flow past anode 10 and then cathode 18. Recovered product means 25 receives the ethylene glycol from reaction cell 7.

As the sodium methoxide and electrolyte passes through cell 7 it goes through the following reaction:

At anode 10 an adsorbed methoxide anion is oxidized to a methoxide radical, i.e.:

$$CH_3O^- \rightarrow CH_3O \cdot$$

wherein two methoxide radicals undergo disproportionation to give formaldehyde and methanol:

$$2CH_3O \cdot \rightarrow CH_2O + CH_3OH$$

The formaldehyde is carried to cathode 18 wherein it is adsorbed onto the surface of cathode 18. Two adsorbed formaldehyde molecules then undergo reductive hydrodimerization to give ethylene glycol, e.g.:

$$2CH_2O \xrightarrow{OH^-} HOCH_2CHO$$

$$HOCH_2CHO \xrightarrow[+2e]{H^+} HOCH_2CH_2OH$$

As an example, a solution containing 1.2M sodium methoxide in methanol containing 0.5 to 1.0% water was electrolyzed at a current density of 30 mA/cm$^2$ in a reaction cell with a separator. Platinum was used as the anode and a graphite pretreated by 10 min. oxidation in H$_2$O$_2$ (30%) was used as a cathode.

The device and process of the present invention as hereinbefore described utilizes an electrochemical single pass two step flowing electrolyte cell to generate ethylene glycol from methanol via intermediate formaldehyde formation.

What is claimed is:

1. A method for forming ethylene glycol from sodium methoxide comprising the steps of:
    combining sodium methoxide with anhydrous methanol to form a mixture,
    flowing the mixture past an anode and then past a cathode, and
    providing a DC voltage across the anode and the cathode so that the mixture yields ethylene glycol.

2. A method for forming ethylene glycol from sodium methoxide comprisng the steps of:
    combining sodium methoxide with anhydrous methanol to form a mixture,
    providing two electrodes,
    providing a direct current electric voltage across both electrodes so that one electrode is positive with respect to the other electrode, and
    flowing the mixture past the one electrode and then past the other electrode so as to form the ethylene glycol from the mixture.

3. A method as described in claim 2 in which the one electrode is an anode made of platinum.

4. A method as described in claim 3 in which the other electrode is a cathode made of pretreated carbon.

5. A method as described in claim 2 in which the one electrode is an anode made of ebonex.

6. A method as described in claim 5 in which the other electrode is a cathode made of pretreated carbon.

7. A method as described in claim 2 in which the one electrode is an anode made of platinum modified titanium.

8. A method as described in claim 7 in which the other electrode is a cathode made of pretreated carbon.

* * * * *